(12) United States Patent
Schmidt et al.

(10) Patent No.: US 9,125,564 B2
(45) Date of Patent: Sep. 8, 2015

(54) SYSTEM, STETHOSCOPE AND METHOD FOR INDICATING RISK OF CORONARY ARTERY DISEASE

(75) Inventors: Samuel Emil Schmidt, Aalborg So (DK); Johannes Jan Struijk, Terndrup (DK)

(73) Assignee: Acarix A/S (DK)

( * ) Notice: Subject to any disclaimer, the term of this patent is extended or adjusted under 35 U.S.C. 154(b) by 0 days.

(21) Appl. No.: 13/994,089

(22) PCT Filed: Dec. 13, 2011

(86) PCT No.: PCT/EP2011/072537
§ 371 (c)(1),
(2), (4) Date: Jun. 13, 2013

(87) PCT Pub. No.: WO2012/080209
PCT Pub. Date: Jun. 21, 2012

(65) Prior Publication Data
US 2013/0261484 A1    Oct. 3, 2013

(30) Foreign Application Priority Data

Dec. 13, 2010  (EP) .................................... 10194756

(51) Int. Cl.
*A61B 5/02* (2006.01)
*A61B 7/04* (2006.01)
*A61B 5/00* (2006.01)

(52) U.S. Cl.
CPC ........... *A61B 5/02007* (2013.01); *A61B 5/7275* (2013.01); *A61B 7/04* (2013.01)

(58) Field of Classification Search
CPC .... A61B 5/7225; A61B 7/045; A61B 5/7275; A61B 5/72; A61B 5/02007; A61B 2562/0204; A61B 7/04
USPC ......................................................... 600/528
See application file for complete search history.

(56) References Cited

U.S. PATENT DOCUMENTS

| | | | |
|---|---|---|---|
| 5,036,857 A | 8/1991 | Semmlow et al. | |
| 5,159,932 A | 11/1992 | Zanetti et al. | |
| 5,638,823 A * | 6/1997 | Akay et al. .................... | 600/528 |
| 6,048,319 A | 4/2000 | Hudgins et al. | |
| 7,096,060 B2 | 8/2006 | Arand et al. | |
| 2006/0282000 A1* | 12/2006 | Zhang et al. .................. | 600/528 |
| 2009/0177107 A1 | 7/2009 | Guion-Johnson | |
| 2010/0160807 A1 | 6/2010 | Schmidt et al. | |

* cited by examiner

*Primary Examiner* — Catherine Voorhees
(74) *Attorney, Agent, or Firm* — Thomas A. Runk; Fulwider Patton LLP

(57) ABSTRACT

A system for detection of frequency power for diagnosing coronary artery disease (CAD), comprising: an acoustic sensor to be placed on the chest of a patient to generate acoustic signals $S_A$; a memory adapted to store acoustic signals $S_A$; a control unit adapted to receive said acoustic signals $S_A$; the control unit comprising: an identification unit to identify diastolic or systolic periods in a predetermined time period and to generate a period signal $S_P$, a filtering unit adapted to apply a filter to said identified periods to generate a low frequency band signal $S_{LFB}$ indicating low frequency bands of identified periods; a calculation unit to estimate the power in said low frequency band of identified periods, to calculate a low frequency power measure and to generate a low frequency power measure signal $S_{LFP}$. The invention also relates to a stethoscope and a method for detection of low frequency power.

18 Claims, 10 Drawing Sheets

SYSTEM, STETHOSCOPE AND METHOD FOR INDICATING RISK OF CORONARY ARTERY DISEASE

RELATED APPLICATIONS

This is a U.S. national phase application PCT/EP2011/072537, filed Dec. 13, 2011, which claims priority to European Application No. 10194756.2, filed Dec. 13, 2010, both of which are incorporated herein by reference.

FIELD OF THE INVENTION

The present invention relates to a system and a method for indicating a risk of coronary artery disease (CAD), and in particular to an electronic stethoscope configured to indicate a risk of CAD from measured acoustic signals.

BACKGROUND OF THE INVENTION

Coronary artery disease (CAD) is a condition in which plaque builds up inside the coronary arteries. These arteries supply the heart muscle with oxygen-rich blood. Plaque narrows the arteries and reduces blood flow to the heart, which can cause angina or a heart attack. Over time, coronary artery disease may weaken the heart muscle and lead to heart failure and arrhythmias. Coronary heart disease is the most common type of heart disease. Lifestyle changes, medicines and/or medical procedures can effectively prevent or treat the disease in most people.

Historically, detection of coronary heart diseases involves patient history, physical examination, stress testing and possibly a coronary angiogram. During physical examination, a stethoscope is often used to examine the sound of the heart. Although the role of the stethoscope in the modern clinic seems to be fading, new electronic stethoscopes with integrated diagnostic algorithms might alter the trend and again expand the clinical potential of the stethoscope. An example of such a type of algorithms is a detector of coronary artery disease.

Four sounds may be generated during each heartbeat. The sounds are produced by blood turbulence and vibration of cardiac structures due primarily to the closing of the valves within the heart. These four sounds are identified as S1, S2, S3 and S4. S1 is usually the loudest heart sound and is the first heart sound during ventricular contraction. S1 is often described as a "lubb" sound. S1 occurs at the beginning of ventricular systole and relates to the closure of atrioventicular valves between the atria and the ventricles. S2 is often described as a "dubb" sound. S2 occurs at the beginning of the diastole and relates to the closing of the semilunar valves separating the aorta and pulmonary artery from the left and right ventricles, respectively. S1 and S2 can be easily heard with a stethoscope ("normal heart sounds"). S3 and S4, however, can usually not be heard in the normal heart ("abnormal heart sounds") of a person over 40 years old. S3, also referred to as "ventricular gallop", occurs in the early diastolic period and is caused by the ventricular wall distending to the point it reaches its elastic limit. S4, also referred to as "atrial gallop", occurs near the end of atrial contraction and is also caused by the ventricular wall distending until it reaches its elastic limit.

Heart sounds can be used to augment the diagnosis and to help assess the severity of important types of cardiac disease. For example, after age 40, S3 can indicate congestive heart failure, and S4 can indicate hypertension, acute myocardial infarction, or coronary artery disease. Unfortunately, studies have shown that even highly experienced physicians do not reliably detect important heart sounds. Therefore various systems have been developed to support physicians in detecting possible heart diseases.

U.S. Pat. No. 7,096,060 relates to a method and system for automatically detecting heart sounds. The sound system may use ECG data to identify various locations, e.g. an R peak, within a beat and use those locations to assist in detection of heart sounds.

U.S. Pat. No. 5,159,932 relates to a myocardial ischemia detection system for non invasively monitoring the motion of the patient's heart, to detect and display ischemia induced variations in the heart's motion which indicate coronary artery disease.

In the system an accelerometer is used as a compression wave transducer which must have a wide bandwidth and should exhibit a flat frequency response from 0.025 Hz to 800 Hz. The purpose of the compression wave transducer is to translate with high accuracy the very low amplitude mechanical motion at the surface of the patient into an electrical signal for further processing. As a result, waveforms including identified morphological features are processed, displayed and used for diagnosis along with a reference ECG.

US-2009/0177107 relates to an electronic stethoscope system that automatically detects coronary artery disease in patients. The system uses an electronic stethoscope to record acoustic data from the fourth left intercostal space of a patient. A processing technique is then applied in order to filter the data and produce Fast Fourier Transform (FFT) data of magnitude versus frequency. If a bell curve is identified in the data between a predefined frequency range (e.g. 50 and 80 Hz) with a peak magnitude of greater than a predefined threshold, e.g. 2.5 units, the system automatically provides an output indicating that the patient is likely to have 50 to 99 percent stenosis of the coronary artery.

Studies have shown that diastolic sounds from CAD patients differ from non-CAD patients. This is described in U.S. Pat. No. 5,036,857. The difference is likely caused by weak murmurs originating from post-stenotic turbulence in the coronary arteries. One method for quantifying the difference in diastolic heart sounds is based on autoregressive (AR) models of the diastolic sounds based upon the fact that the pole magnitudes in AR-models of the diastolic heart sound in CAD patients differed from non-CAD patients.

U.S. Pat. No. 6,048,319 relates to a non-invasive acoustic screening device for detecting coronary stenosis by identifying S1 and S2 heart sounds, heart rate, and determines the diastolic interval of the subject and thereafter estimates the acoustic energy levels within a 2 octave band around approximately 20 Hz during diastole. Based upon such estimation, a diagnosis can be rendered as to the presence and degree of stenosis from the coronary artery.

Originally, the weak sounds were collected using very sensitive custom-made sensors, but the advent of electronic stethoscopes offers new opportunities. Advances of the electronic stethoscopes are portability, low cost and ease of use. The potential of implementing a CAD detection algorithm in electronic stethoscopes would yield an easily applicable CAD test. However the CAD related murmurs are very weak and the difference between CAD and non-CAD sounds is small. Detection algorithms are, therefore, likely to be sensitive to other types of noise, such as ambient noise and physiological noise, which will limit the usability of the method.

Based upon studies of the noise sensitivity of AR-models, when the models were applied for identification of CAD patients by analysis of heart sound recordings from an electronic stethoscope, the inventors have identified a need for improvement of the currently used analysis methods.

Thus, the object of the present invention is to provide an improved analysis system and method in order to improve diagnosis of CAD.

SUMMARY OF THE INVENTION

The above-mentioned object is achieved by a system for detection of frequency power comprising an acoustic sensor adapted to be placed on the chest of a patient. The system further comprises: at least one memory adapted to store acoustic signals $S_A$ from the acoustic sensor; and a control unit adapted to receive said acoustic signals $S_A$ according to the first independent claim. The parts of the system can be placed separately, e.g. the sensor and memory may be part of an electronic stethoscope capable of sending recorded data to an external unit comprising said control unit, for further processing of the data.

According to another aspect the object is achieved by an electronic stethoscope comprising an acoustic sensor adapted to be placed over a patient's chest, a memory and a control unit according to the invention. Thus, a compact stethoscope is achieved with the capability of indicating a risk of CAD. Advances of the electronic stethoscopes are portability, low cost and ease of use. The implementation of a CAD detection algorithm in electronic stethoscopes yields an easily applicable CAD test.

According to a further aspect, the object is achieved by a method for detecting frequency power using a system for detection of frequency power. In particular, the method according to the invention can be used to improve other methods for diagnosing CAD.

The detection of low frequency power in relation to coronary artery disease (CAD) comprises the following steps:
  recording acoustic data with an electronic stethoscope having an acoustic sensor placed on the chest of a patient, and generating acoustic signals $S_A$ indicating said data;
  identifying diastolic or systolic periods in a predetermined time period of the stored acoustic data, and generating a period signal Sp indicating said identified periods;
  applying at least one filter to the period signal Sp and generating a low frequency band signal $S_{LFB}$ indicating low frequency bands of said identified periods;
  estimating the power in said low frequency band of said identified periods;
  calculating a low frequency power measure based upon said estimated power, and generating a low frequency power measure signal $S_{LFP}$ indicating said low frequency power measure.

The low frequent components of the heart sounds are most likely related to movements of the ventricle.

Preferred embodiments are set forth in the dependent claims.

The estimation of the power in the low frequency band in the diastolic or systolic periods can be estimated using one of the following methods:
  Band pass filter the signal using a 5-70 Hz, preferably 10-60 Hz, more preferably 15-50 Hz, and most preferably 20-50 Hz band pass filter frequency and calculate the variance in the periods.
  Generate a power spectrum (directly or indirectly by AR-models) of the periods and calculate the power related low frequency band.

A median low frequency band power is preferably calculated for several heart-beats. The low frequency power measure may also be corrected against differences caused by body mass index (BMI), gender, age, disease or similar estimates of the tissue dampening factor. A risk of CAD may then be determined by comparing the low frequency power measure with a reference value. An increased low frequency power measure compared to the reference value is according to studies an indication that the patient has CAD.

Recent studies according to the examples in the description demonstrated that diastolic heart sounds, recorded with an electronic stethoscope, contain markers of CAD, but the CAD-related sound is very weak and recordings are often contaminated by noise. The current study according to the examples analyses the noise contamination of 633 stethoscope recordings from a clinical environment. Respiration noise, ambient noise, recording noise and abdominal noise were identified in the recordings and were classified according to duration and intensity. To monitor how noise influences the classification performance of a common classification algorithm, AR-pole magnitudes were extracted from both the 25-250 Hz frequency band and the 250-1000 Hz frequency band. The classification performance was quantified by the Area Under the receiver operating Characteristic (AUC). Ambient noise was present in 39.9% of the recordings and was the most common noise source. Abdominal noise was the least common noise source, present in 10.8% of the recordings. The best pole, with respect to detection of CAD, extracted from the 250-1000 Hz frequency band was most sensitive to noise, since the AUC dropped from 0.70 in recordings without noise to 0.57 when noisy recordings were included, whereas the best pole from the 25-250 Hz frequency band was relatively robust against noise, since the AUC dropped from 0.73 to only 0.70 when noisy recordings were included. The study according to the examples in the description demonstrated that noise contamination is a frequent problem and that features from lower frequency bands are more robust against noise than features from higher frequency bands.

Both low frequency and high frequency sounds are produced during the normal heart cycle. Increased high frequency heart sounds have been found associated with coronary artery disease and originating from the vibrating stenosed coronary arteries. Increased low frequency heart sounds have not been found to originate from the stenotic coronary arteries, and are as such independent in origin.

Surprisingly, the combination of a low-frequency power spectrum and a high-frequency power spectrum could provide an even more certain coronary artery disease diagnosis, than either the low frequency power spectrum or the high frequency power spectrum alone. The low frequency signals are less sensitive to disturbances than the high frequency signals, thus, information may be retracted from the low frequency signals that is not possible from the high frequency signals contributing to a more secure and accurate diagnose of CAD.

SHORT DESCRIPTION OF THE APPENDED DRAWINGS

Below the invention will be described in detail with reference to the appended figures, of which:

DETAILED DESCRIPTION OF PREFERRED EMBODIMENTS OF THE INVENTION

Figure 1:
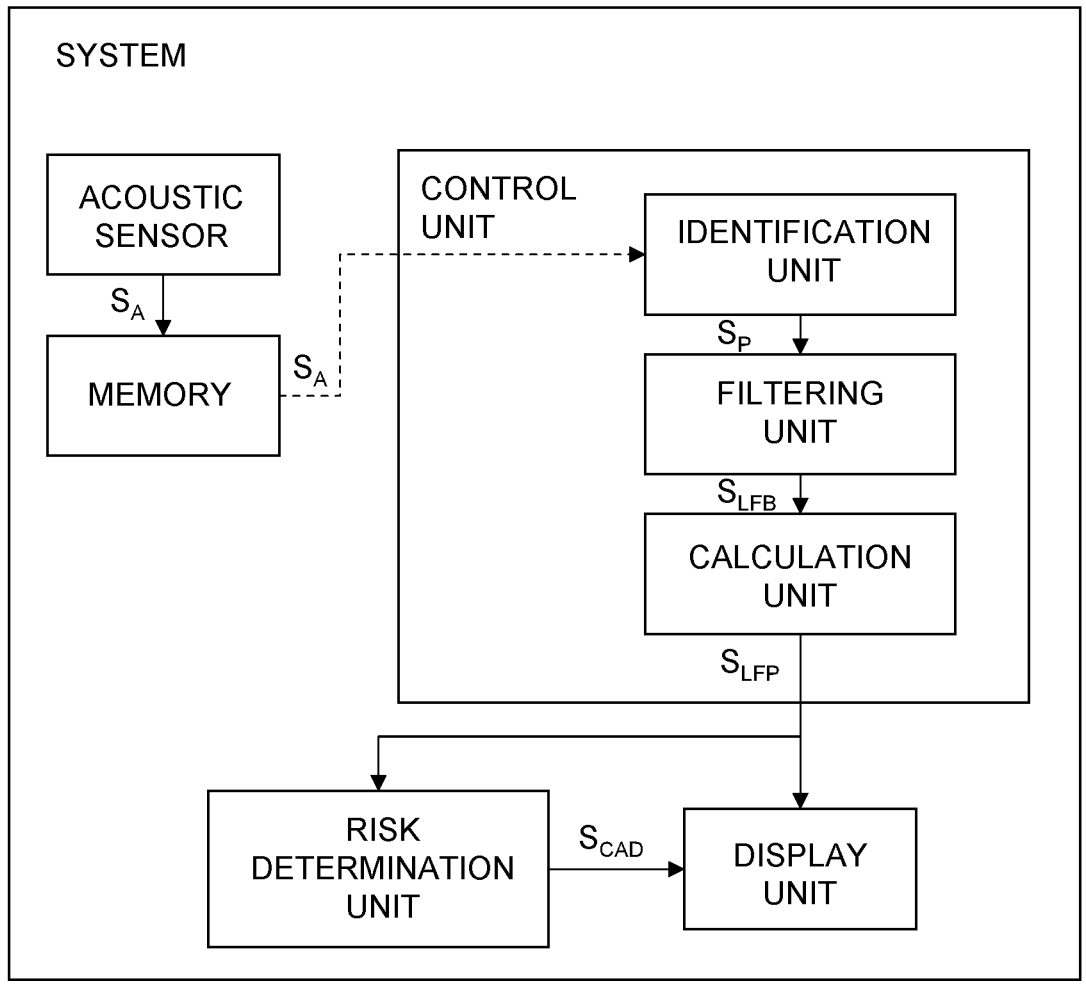
FIG. 1 illustrates a system according to one embodiment of the invention.

FIG. 1 shows a system for detection of frequency power according to the invention. The system can be used for diagnosing of coronary artery disease (CAD), and in particular for classification of CAD together with other indicators. For sensing of acoustic sound waves, the system comprises an acoustic sensor adapted to be placed on the chest of a patient, and to generate acoustic signals $S_A$. The acoustic sensor comprises e.g. a microphone, an accelerometer or an optical beam device. The sensor may according to one embodiment be adapted to sense acoustic sounds down to 5 Hz. According to another embodiment, the sensor is adapted to sense acoustic sounds down to 20 Hz. The system further comprises at least one memory adapted to store acoustic signals $S_A$ from the acoustic sensor; and a control unit adapted to receive said acoustic signals $S_A$. According to one embodiment, the acoustic sensor and the memory are incorporated in a separate device e.g. an electronic stethoscope adapted to transmit the sensed acoustic signals by wire or wirelessly to an external unit comprising said control unit. Thus, at least parts of the system are according to this embodiment embodied by an electronic stethoscope. The separate device, i.e. the stethoscope, then comprises a transmitting unit adapted to transmit the signals (not shown in the figure). The signals may be processed in the external unit instead of in the stethoscope. According to one embodiment, the memory is a detachable memory such as a USB-device, which can be plugged into the external unit.

The control unit comprises an identification unit adapted to identify diastolic or systolic periods in a predetermined time period of the stored acoustic signals $S_A$, and to generate a period signal $S_P$ indicating the identified periods. The predetermined time period may include a predetermined number of diastolic or systolic periods. The previous mentioned S2-sound occurs in the beginning of the diastolic period and relates to the closing of the semilunar valves separating the aorta and pulmonary artery from the left and right ventricles, respectively. The S1-sound occurs in the beginning of ventricular systole and relates to the closure of atrioventicular valves between the atria and the ventricles.

The control unit further comprises a filtering unit adapted to apply at least one filter to the identified periods and to generate a low frequency band signal $S_{LFB}$ indicating low frequency bands of the identified periods. The filtering unit may also be applied when the filtering is performed by using the power spectrum density (PSD) method (as discussed in example 8) if the low frequency energy is estimated using PSD where at least one filter is applied to said identified periods and to empathize frequencies relevant for estimation of low frequency power.

The heart sounds in the lower frequency range of the periods have according to studies shown to be less sensitive to disturbances than the heart sounds in other frequency ranges. According to one embodiment, the low frequency band in between 5-70 Hz, preferably 10-60 Hz, more preferably 15-50 Hz and most preferably 20-40 Hz.

From the low frequency band a low frequency power measure can be derived. Findings from studies have shown that the amplitude of the low frequency part of the period signal $S_P$ was increased in the CAD patients, thus indicating a change in the ventricle compliance. This information is useful as a feature in multivariate classification of CAD, and can be combined with more high frequent features which are related to CAD murmurs. See e.g. patent application US 2010160807 A1.

For estimating the power, the control unit comprises a calculation unit adapted to estimate the power in the low frequency band of the identified periods. According to one embodiment, the control unit is adapted to estimate the power by band pass filtering said identified periods using a 5-70 Hz, preferably 10-60 Hz, more preferably 15-50 Hz, and most preferably 20-40 Hz band pass filter frequency and calculating the variance during said periods. Thus, the filtering unit band pass filters the identified periods with a between 5-70 Hz, preferably 10-60 Hz, more preferably 15-50 Hz and most preferably 20-40 Hz band pass filter frequency, and the calculation unit calculates the variance during the band pass filtered period. The calculated variance is named low frequency power.

The examples 1-7 relate to results from two different studies, one study based on recordings obtained using a standard electronic stethoscope (3M Littmann E4000) and another study using a custom made sensor adapted to sense low frequencies.

Example 1

Figure 3:
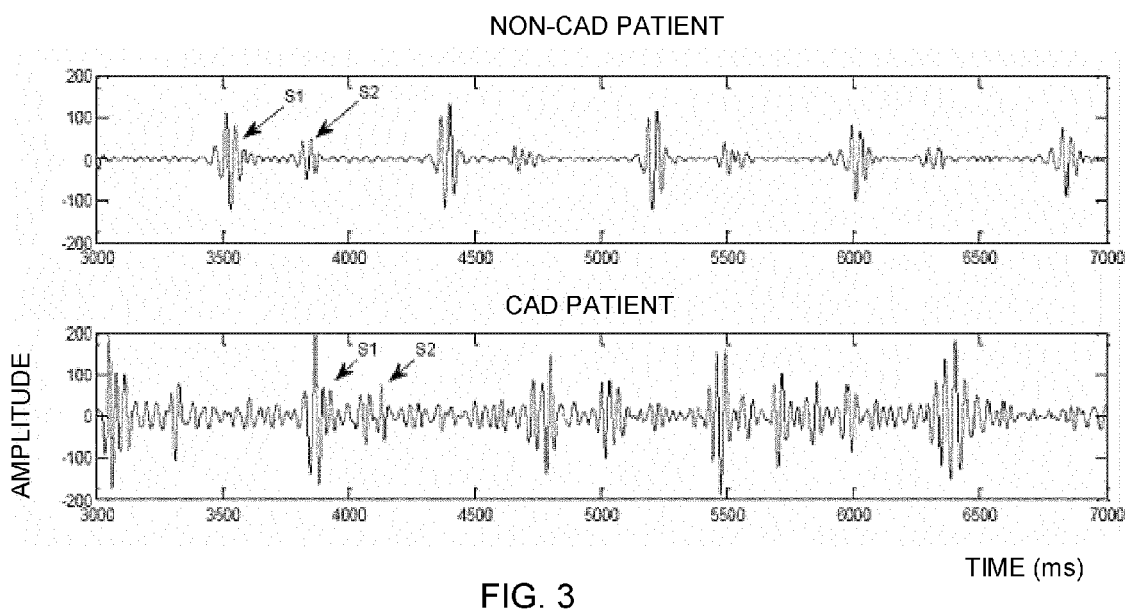
FIG. 3 shows two band pass filtered heart sound recordings from a non-CAD patient (on top) and a CAD patient (below).

FIG. 3 shows recordings of heart sounds with an electronic stethoscope of two different patients, filtered with a 20 to 50 Hz band pass filter. The top chart shows recordings from a non-CAD patient, and the lower chart shows recordings from a CAD patient. The recordings are from two males with approximately the same body mass index (BMI). As can be seen from the charts, the amplitude in both systole (S1) and diastole (S2) increased in the CAD patient.

According to another embodiment, the calculation unit is adapted to estimate the power by generating a power spectrum directly or indirectly with at least one auto-regressive (AR)—model of the low frequency band and calculate the power in the low frequency band. A power spectrum can be calculated directly by calculating using Fast Fourier Transform (FFT), and indirectly by calculating the power spectrum from a model of the signal. An autoregressive model can be viewed as the output of an all-pole infinite response filter whose input is white noise. The pole magnitudes in AR-models of the diastolic heart sounds in CAD patients have been found to differ from non-CAD patients. For example, a sub-segmentation method can be used to extract the pole-magnitude of the AR-model(s).

Example 2

In the study according to the examples, a sub-segmentation method was used. The pole-magnitudes of the AR-models were extracted from the diastolic segments. The sub-segmentation method divided the diastolic periods into sub-segments of short duration and removed sub-segments with high variance, before the AR-pole magnitudes were calculated from the remaining sub-segments. The sub-segmentation method improved the robustness against noise of short duration, such as friction spikes. AR-models with order 2, 4, 6, 8 and 10 were constructed using the foreword backward method. The pole magnitude which obtained the best classification performance in recordings without insignificant noise was selected for the evaluation of the classification performance for all signals. Early studies of heart sounds from CAD patients focused mainly on frequencies above 200 Hz since CAD was associated with an increase in spectral energy above 250 Hz, whereas recent studies include lower frequencies. Therefore, the AR-pole magnitudes were extracted from the 25-250 Hz frequency band as well as the 250-1000 Hz frequency band. The frequency bands were created using 8th-order Chebyshev band pass filters.

The performances of the AR-poles were evaluated by calculating the Area Under the receiver operating Characteristic (AUC). The AUC was evaluated under different maximum allowable levels of noise intensity and durations.

From the 25-250 Hz frequency band the best performing feature was the pole magnitude of the first pole in the 6 order AR model. The AUC for the "clean recordings" was 0.725, and dropped to 0.7 when all noisy recordings were included. The results indicate that the noise does not affect the AUC considerably when the 25-250 Hz band was used. Only when the noise exceeds 4 seconds a slight drop in AUC is observed for respiration noise and ambient noise. Therefore, the recommended noise threshold is maximum 4 seconds for respiration noise and ambient noise. 458 of the recordings fulfill these criteria and the AUC was 0.725 if the criteria were applied. The robustness to noise and the AUC performances of the pole extracted from the 25-250 Hz frequency band indicate that features extracted from the lower frequencies of the heart sounds are most suitable for detection of CAD markers if the heart sounds are recorded with a handheld electronic stethoscope in a clinical environment.

The study according to the examples demonstrates that noise contamination of heart sound recordings is a widespread problem when recordings are collected with an electronic stethoscope in a clinical environment. Both pole magnitudes from AR-models of the 25-250 Hz frequency band and the 250-1000 Hz frequency band allowed reasonable classification between CAD and non-CAD subject, but only the pole extracted from the 250-1000 Hz frequency band was very sensitive to noise.

The calculation unit is further adapted to calculate a low frequency power measure based upon the estimated power and to generate a low frequency power measure signal $S_{LFP}$ indicating said low frequency power measure. According to one embodiment, the low frequency power measure is determined by calculating the median low frequency power of several heart beats, i.e. of several identified diastolic or systolic periods. Thus a measure of the low frequency power is obtained, which value indicates if the patient is suffering from CAD.

Example 3

Figure 4:
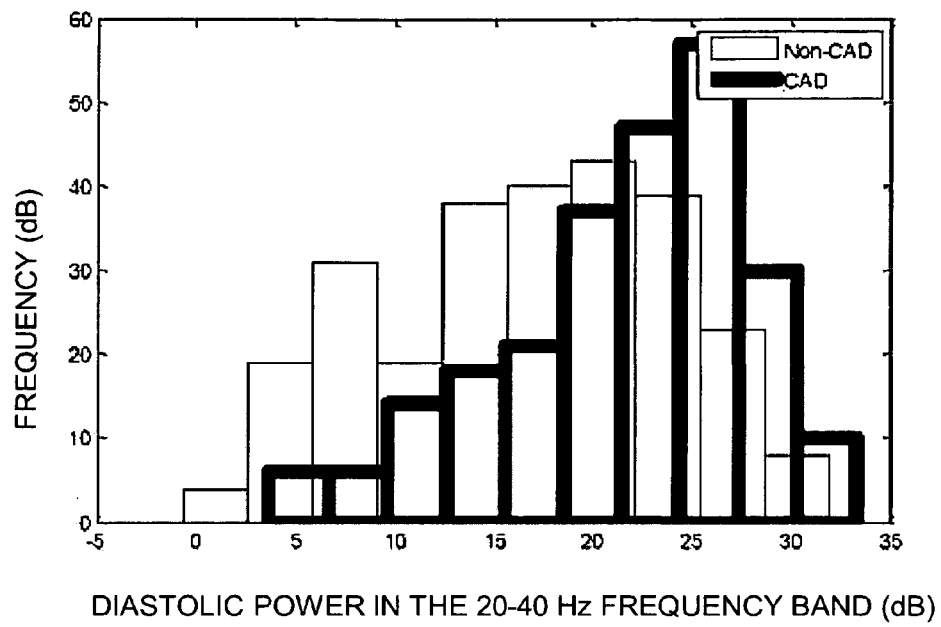
FIG. 4 shows a histogram of low frequency power in CAD and non-CAD patients, respectively, from a stethoscope study according to the examples in the description.

The histogram in FIG. 4 shows the diastolic power in the 20 to 40 Hz frequency band in 264 recordings from 70 non-CAD subjects and 246 recordings from 63 CAD subjects, from the study according to the examples with an electronic stethoscope. The power was calculated by filtering the recordings with a 20 to 40 Hz band pass filter and calculating the variance in the diastoles. The feature is named low frequency power. The classification performance of the low frequency energy is measured with the area under the receiver operating characteristic curve (AUC). The AUC of the 20-40 Hz diastolic power was 69.44%. The mean power in the 20-40 Hz frequency band was 16.8 dB (STD=7.3) for the non-CAD patients and 21.7 dB (STD=6.2) for the CAD patients.

Example 4

Figure 5:
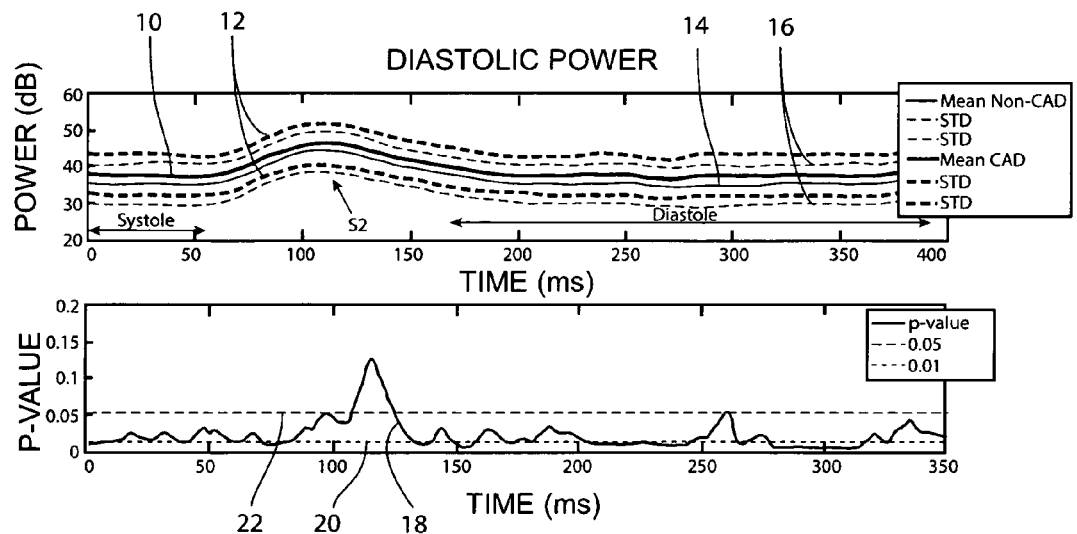
FIG. 5 shows the mean power calculated using a running variance. The lower diagram shows P-values used for determining the significance of the power difference.

FIG. 5 shows the mean power 10 with standard deviation 12 for a group of CAD patients and the mean power 14 with standard deviation 16 for a group of non-CAD patients. The mean powers 10 and 14 are calculated using a running variance in end-systole and start-diastole and are obtained with the custom made sensor. The lower window shows the P-values 18 used for determining the significance of the power difference between the two groups of CAD patients and non-CAD patients, respectively. A P-value of 0.05 is indicated by the dashed line 20 and a P-value of 0.10 is indicated by the dashed line 22. The P-values 18 are calculated using a T-test. As seen, the power difference is significant (5%) in both diastole and systole, but not at the time when the S2 is present.

According to one embodiment, the system comprises a display unit adapted to indicate the low frequency power measure.

Example 5

Figure 6:
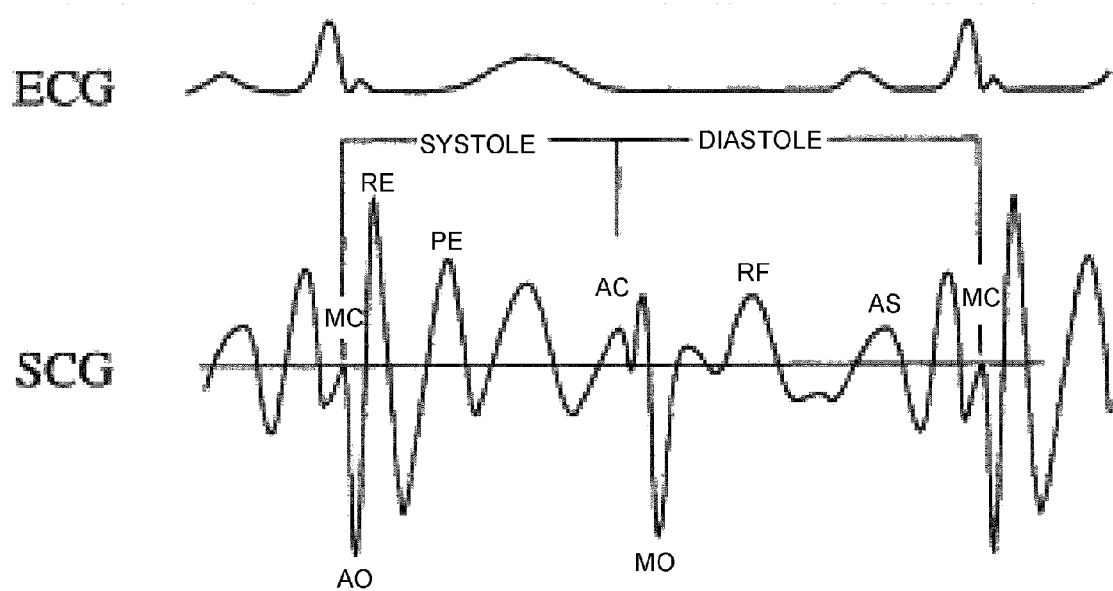
FIG. 6 shows simultaneously recorded seismocardiogram (SCG) and electrocardiogram (ECG) with timing of seismocardiographic waves during cardiac cycles.

FIG. 6 shows simultaneously recorded seismocardiogram (SCG) and electrocardiogram (ECG) with timing of seismocardiographic waves during cardiac cycle. Based on Doppler mode and M-mode echocardiographic studies, systolic events were identified as mitral valve closure (MC), isovolumic movement (IM), aortic valve opening (AO), rapid systolic ejection (RE) and aortic valve closure (AC). Diastolic events include mitral valve opening (MO), early rapid filling (RF) and atrial systole (AS).

To be able to indicate for a practitioner that a patient is likely to suffer from CAD, the system comprises according to one embodiment a risk determining unit adapted to determine a risk of CAD by comparing the low frequency power measure with at least one reference value for CAD, and generating a risk-of-CAD-signal $S_{CAD}$ indicating the result of said comparison. The result may be indicated on the display unit, thus, the display unit 30 is according to one embodiment adapted to indicate said risk of CAD.

The inventors have found that the combination of a low-frequency power spectrum and a high-frequency power spectrum provides an even more certain coronary artery disease diagnosis, than either the low frequency power spectrum or the high frequency power spectrum alone. This embodiment is illustrated by the schematic block diagram in FIG. 2.

According to this embodiment, the filtering unit is adapted to apply a filter to said identified periods and to generate a high frequency band signal $S_{HFB}$ indicating high frequency bands of said identified periods. According to one embodiment, the high frequency band is between 250-1000 Hz. In addition to calculating a low frequency power measure, the calculation unit according to this embodiment adapted to calculate a high frequency feature measure based upon an estimated feature in high frequency bands of said periods and to generate a high frequency feature measure signal $S_{HFF}$ indicating said high frequency feature measure. The risk determining unit is then in addition adapted to compare said high frequency feature measure with a further feature reference value for CAD and to generate a combined risk-of-CAD-signal $S'_{CAD}$ indicating said risk in dependence of said comparison. Features from high frequency bands can be of different types such as power, power ratio or complexity. For different features, different feature reference values for CAD are used. Thus, an even more certain coronary artery disease diagnosis is then achieved.

Figure 2:
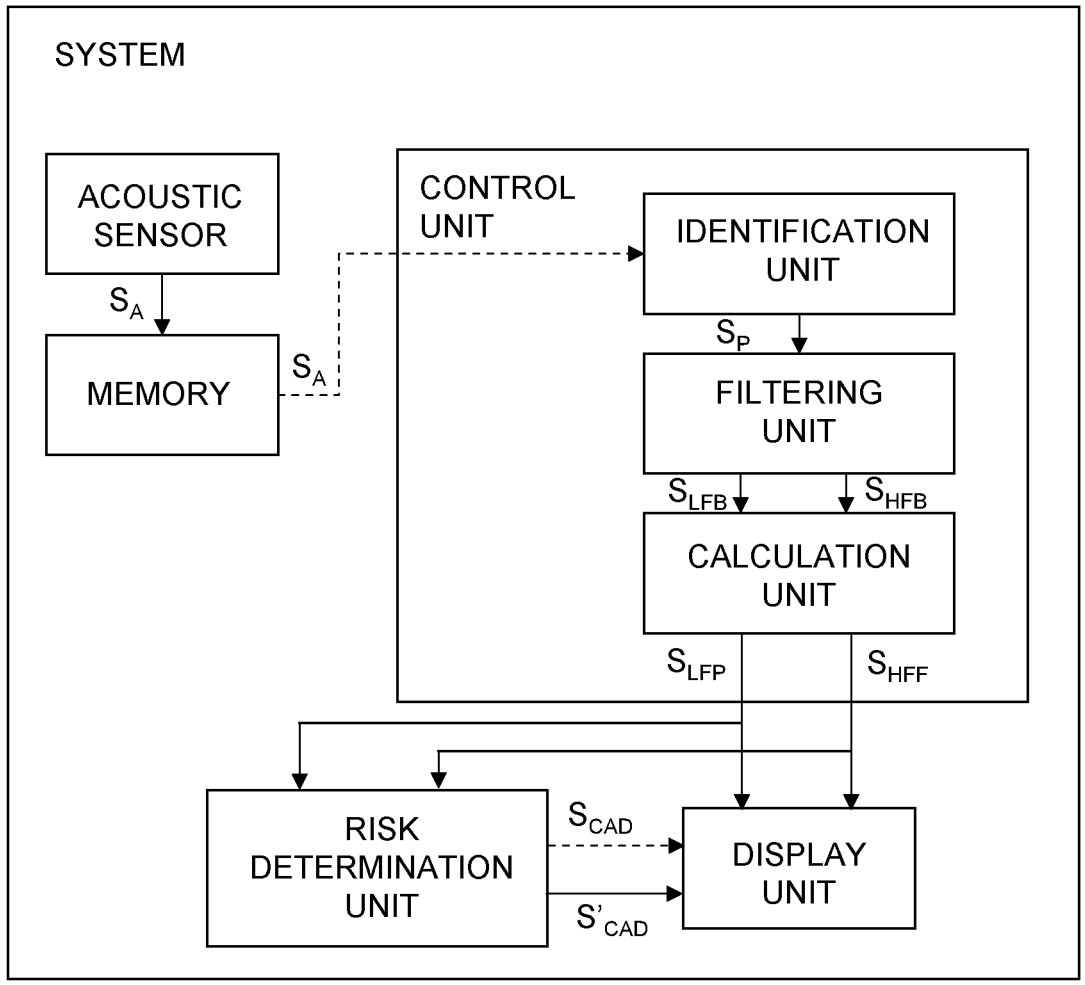
FIG. 2 illustrates a system according to another embodiment of the invention.

Thus, it is naturally possible, within the scope defined by the present claims, to generate $S'_{CAD}$ alone or $S_{CAD}$ (illustrated by FIG. 1) alone or both signals at the same time which is illustrated by FIG. 2.

The amplitude of the recordings may be affected by tissue damping factors. To provide accurate sensor values, the calculation unit is accorded to one embodiment adapted to correct the low frequency power measure against at least one tissue damping factor, such as body mass index (BMI), gender, age and disease.

Example 6

The amplitude of the low frequency recordings is most likely to be related to BMI, since the distance from the ventricle to the recording spot will affect the amplitude. In a study according to the examples using the electronic stethoscope, the BMI was known in 66 subjects. A negative correlation between the BMI and the power in the 20-40 Hz band was shown. The correlation between BMI and low frequency power in healthy subjects was in this study r=−0.27.

The influence of the BMI can be corrected using a linear correction:

corrected low frequency power=low frequency power+0.43·BMI+11.6    (1)

In the 66 subjects where BMI was available, the classification performance AUC was 72.6% before correction and 73.1%) after correction. Thus, the accuracy of the low frequency power was improved.

Example 7

The low frequency power score is likely to be related to gender since the women's heart is smaller and the breasts increase the distance from the ventricle to the recording spot. In the electronic stethoscope study according to the examples, the mean female low frequency power was 13.9 dB in the healthy patients and 15.8 dB in the diseased female patients, when mean power was respectively 20.3 dB and 23.4 dB for the males. This clearly demonstrates that the power levels are lower in the female group compared to the male group. The classification performance was AUC=68.4% in the male group and 58% in the female group.

According to one embodiment, the influence of gender is corrected to remove the difference between the results between men and women. If the influence is not corrected for, different reference values for the low frequency power measure should be used for men and women respectively.

It has further been observed that the diastolic low frequency power strongly correlates to the systolic low frequency power in the CAD-recordings. According to one embodiment, the calculation unit is adapted to calculate low frequency power measures for both diastolic and systolic periods, to compare the measures and generate a correlation value based upon the comparison indicating the correlation between the low frequency power measures. Thus, if the values correlate, this is indicated in the correlation value and supports the assumption that a patient has CAD.

Example 8

Power generated by low frequency components, in this case in the frequency band 10-90 Hz, of the heart signal can be more precisely estimated by normalizing the generated power over other, higher frequency band. In the current example, this larger frequency band is 90-300 Hz. This power ratio PR may be expressed as:

$$PR = \frac{\sum_{10}^{90} PSD(f)}{\sum_{90}^{300} PSD(f)}$$

Where PSD is the power spectrum density.

Accordingly, the power generated in the low frequency band is normalized against the power of the higher frequency band, i.e. power ratio of the two power values is calculated. In this way, noise and/or variations between individuals may be removed. FIG. 6 shows, as expected, that the averaged diastolic power value for CAD-patients in low frequency band is greater than corresponding value of the control group.

One problem when applying PSD is that the dynamic range of PSD is high, approximately 70 dB, meaning that the low frequency part of the signal is 70 higher than the high frequency part of the signal. Therefore the HF part of the signal is covered by the LF part. This is due to a phenomena called spectral leakage. By adjusting a so-called whitening filter to make the PSD of average healthy subject white, all frequencies will have the same power. Thereby the dynamic range of the frequency spectrum is reduced, which will reduce spectral leakage, and thereby it will be possible to estimate low frequency power and high frequency power from the same spectrum.

Figure 7:
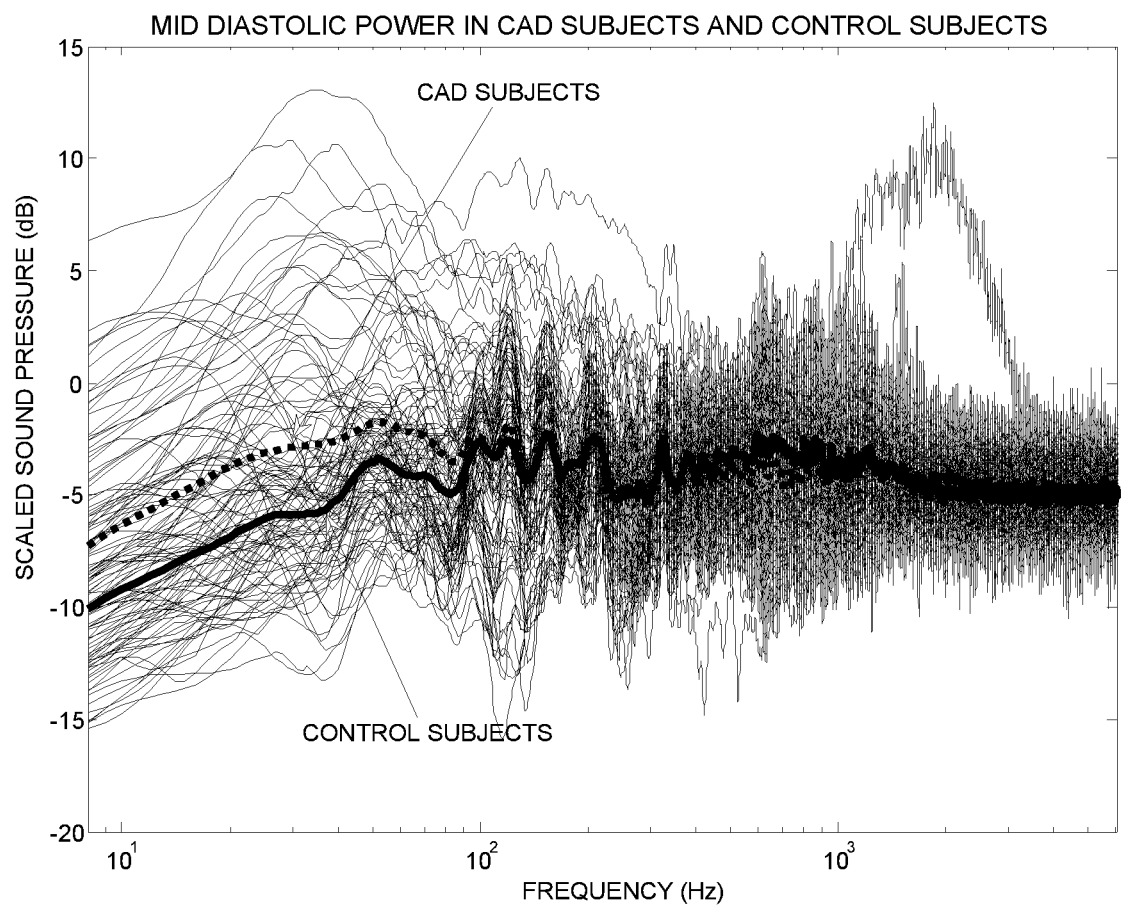
FIG. 7 shows mid diastolic power in CAD subjects and control subjects.

In a sample of FIG. 7 comprising 112 patients, the area under the curve is 78.21%. Moreover, if threshold is defined, a sensitivity of 73.42% and specificity of 75.76% is obtained.

Example 9

The example shows that by combining the estimated power ratio obtained in the previous example 8 (i.e. by normalizing power obtained in the frequency band 10-90 Hz over power obtained in the frequency band 90-300 Hz) with the analogously obtained, estimated power ratio in respectively 700-900 Hz and 900-1300 Hz frequency band, an improved classification model is obtained.

Figure 8:
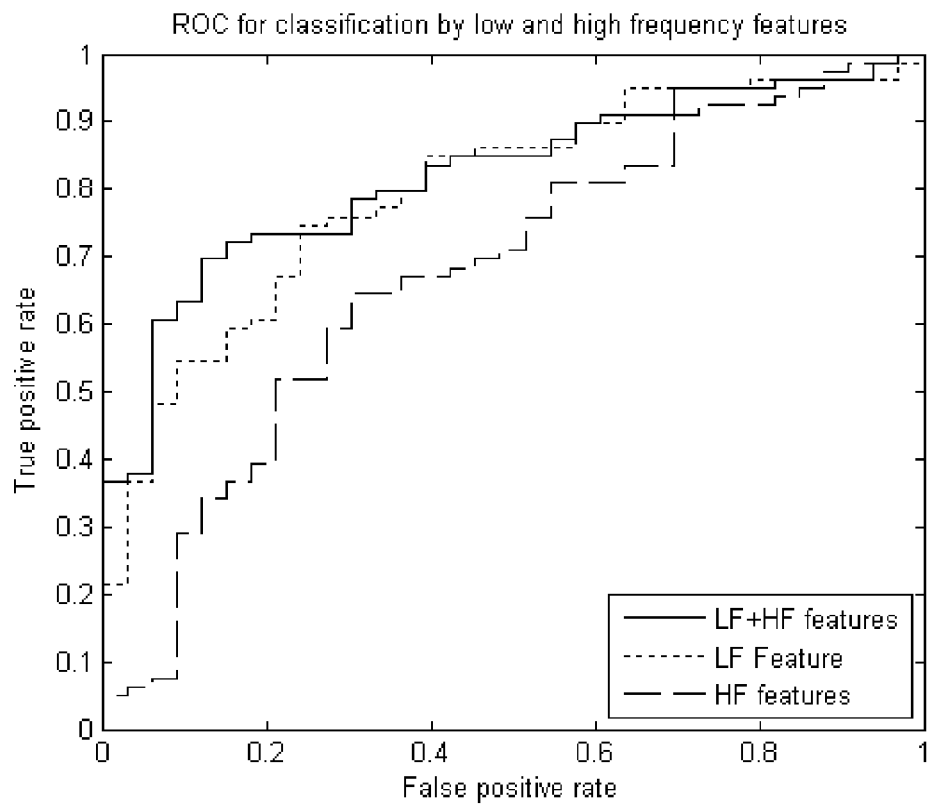
FIG. 8 shows the combined estimated power ratio of example 8.

More specifically, in a sample comprising 112 patients and being visualized by means of a ROC space shown in FIG. 8, Area Under Curve (AUC) is 67.6% for the latter estimated power ratio alone, and for the combined score of both estimated power ratios, the AUC is, using a quadratic discriminating function, 81.1%.

Figure 9:
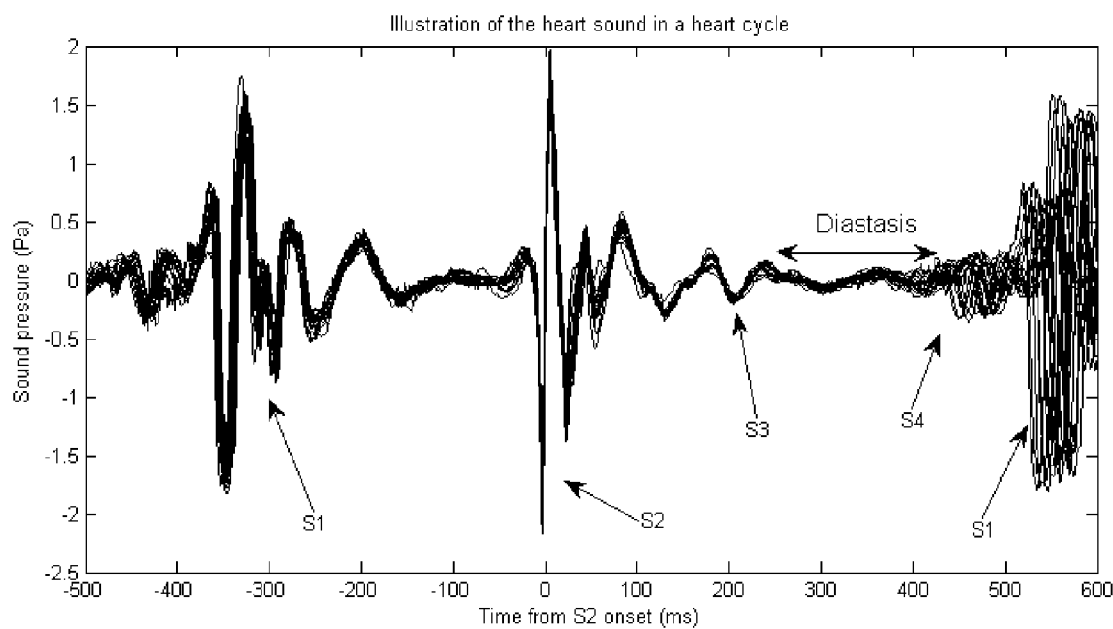
FIG. 9 illustrates a specific period of the heart sound signal.

According to a further refinement of the present invention, which is based upon the findings that the power in the low frequency band may be measured in different ways. It may, for instance, be measured in a predefined time interval of the diastole starting 200-300 ms after the S2 sound. One way to perform the measurement is then to, in each individual recording, identify a time interval named "diastasis", which is the last stage of diastole, i.e. time period between S3 and S4 sounds. Since diastasis is, as it may also be seen in FIG. 9, a relatively quiescent period, one way to do this is to identify the time window in the diastole with the lowest power. This time window might be 100 ms or longer and is found in the interval from approximately 200 ms after the S2 and 100 ms before S1, but not later than 450 ms after S2.

Figure 10:
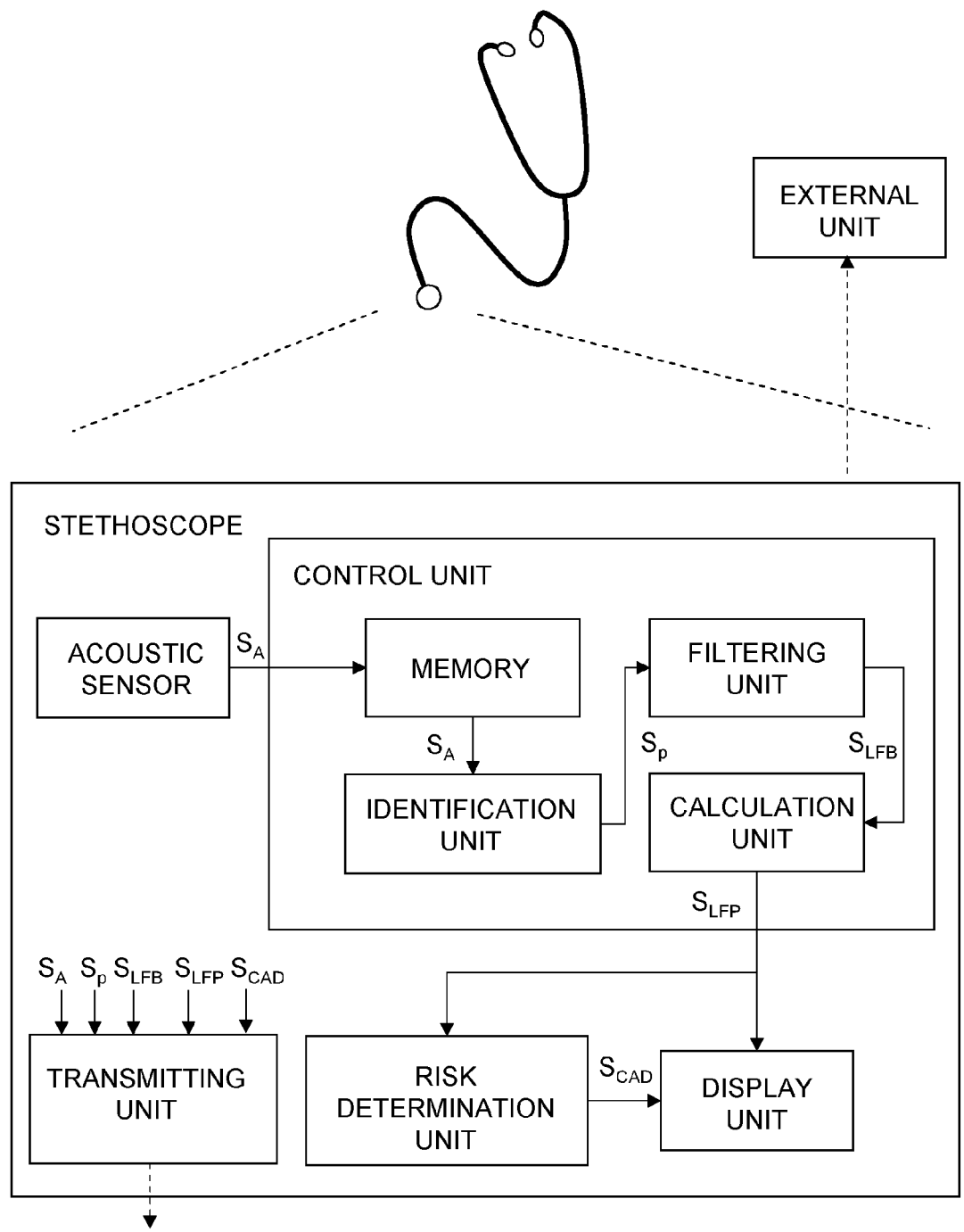
FIG. 10 illustrates an electronic stethoscope according to one embodiment of the invention.

According to one embodiment, the invention relates to an electronic stethoscope as shown in FIG. 10. The electronic stethoscope is adapted to convert acoustic sound waves to electrical signals which can be further processed. For sensing of acoustic sound waves, the stethoscope comprises an acoustic sensor adapted to be placed on the chest of a patient, and to generate acoustic signals $S_A$. The stethoscope further comprises at least one memory adapted to store acoustic signals $S_A$ from the acoustic sensor; and a control unit adapted to receive said acoustic signals $S_A$. Because the sounds are transmitted electronically, the electronic stethoscope can be a wireless device, a recording device, and may provide noise reduction, signal enhancement, and both visual and audio output. According to one embodiment, the electronic stethoscope comprises a transmitting unit adapted to transmit the signal(s) referred to herein to an external unit. Thus, the signals can be further used and processed in another unit. The control unit comprises an identification unit adapted to identify diastolic or systolic periods in a predetermined time period of the stored acoustic signals $S_A$, and to generate a period signal Sp indicating said identified periods; a filtering unit adapted to apply at least one filter to said identified periods and to generate a low frequency band signal $S_{LFB}$ indicating low frequency bands of said identified periods; and a calculation unit adapted to estimate the power in said low frequency band of said identified periods, to calculate a low frequency power measure based upon said estimated power and to generate a low frequency power measure signal $S_{LFP}$ indicating said low frequency power measure.

The functions of the units in the stethoscope are the same as in the system according to the invention. For example, the stethoscope may comprise a risk determining unit adapted to determine a risk of CAD by comparing the low frequency power measure with at least one reference value for CAD, and generating a risk-of-CAD-signal $S_{CAD}$ indicating the result of the comparison. The stethoscope comprises according to one embodiment a display unit adapted to indicate said low frequency power measure and/or the result of the above-mentioned comparison, e.g. the patient's risk of CAD. It should be noted that the stethoscope also may be provided with the necessary means required to generate the combined risk-of-CAD-signal $S'_{CAD}$, i.e. the means described e.g. in connection with the embodiment illustrated by FIG. 2.

Figure 11:
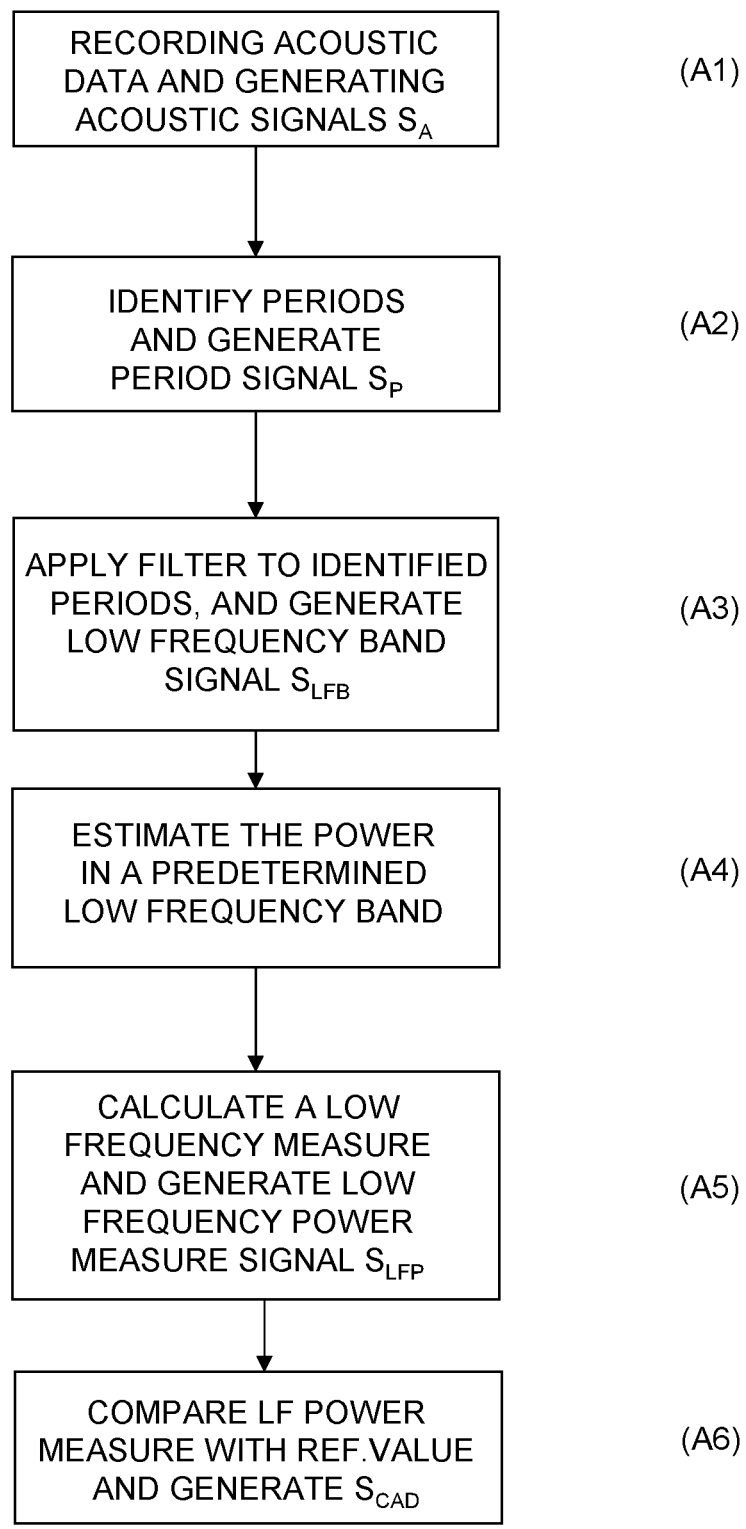
FIG. 11 shows a flow chart of a method according to one embodiment of the invention.

The invention also relates to a method for detecting frequency power for diagnosing of coronary artery disease (CAD) using a system according to the invention. The different steps in the method will now be explained with reference to the flow chart in FIG. 11.

The method comprises the first step A1 of recording acoustic data with a system for detection of frequency power comprising an acoustic sensor placed on the chest of a patient, and generating acoustic signals $S_A$ indicating said data. The sensor is preferably placed closely to the patient's heart, to be able to sense and record sound from heart beats. The most significant sounds of the heart are referred to as S1, S2, S3 and S4 as has been explained in the preceding text.

In a second step A2 diastolic or systolic periods are identified in a predetermined time period of the stored acoustic data, and a period signal $S_P$ indicating said identified periods is generated. Thus, the duration of the diastolic or systolic periods is identified. According to one embodiment, only the diastolic or systolic periods are present in the period signal $S_P$.

In a third step A3, at least one filter is applied to the period signal $S_P$ and a low frequency band signal $S_{LFB}$ is generated indicating low frequency bands of the identified periods. Preferably frequencies above 100 Hz are filtered away. According to one embodiment, the period signal Sp is band pass filtered using a 5-70 Hz, preferably 10-60 Hz, more preferably 15-50 Hz, and most preferably 20-40 Hz band pass filter frequency.

In a fourth step A4, the power in the low frequency band of said identified periods is estimated. The estimation may according to one embodiment be performed using one of the two following methods:
1. Estimating the power by band pass filtering said identified periods using a 5-70 Hz, preferably 10-60 Hz, more preferably 15-50 Hz, and most preferably 20-40 Hz band pass filter frequency and calculating the variance during said periods.
2. Estimating the power by generating a power spectrum directly or indirectly with at least one AR-model of said low frequency band and calculating the power in said low frequency band.

In a fifth step A5, a low frequency power measure is calculated based upon said estimated power, and a low frequency power measure signal $S_{LFP}$ is generated indicating said low frequency power measure.

For determining a risk of CAD, the method comprises according to one embodiment the step (A6) of comparing said low frequency power measure with at least one reference value for CAD, and generating a risk-of-CAD-signal $S_{CAD}$ indicating the result of said comparison. The risk of CAD may be shown on a display, or audibly transmitted to the practitioner.

The method comprises according to one embodiment the steps of:
applying a filter to the period signal Sp and generating a high frequency band signal $S_{HFB}$ indicating high frequency bands of said identified periods;
estimating a feature in said high frequency bands of said identified periods;
calculating a high frequency feature measure based upon the estimated feature in high frequency bands of said periods, and generating a high frequency feature measure signal $S_{HFF}$ indicating said high frequency feature measure, and comparing said high frequency feature measure with a further feature reference value for CAD and generating a combined risk-of-CAD-signal $S'_{CAD}$ indicating said risk in dependence of said comparison. Features from high frequency bands can be of different type such as power, power ratio or complexity. Thus, an even more certain coronary artery disease diagnosis may be achieved.

According to another embodiment the present invention relates to a method for detecting frequency power for diagnosing of coronary artery disease (CAD) using a system for detection of frequency power.

Figure 12:
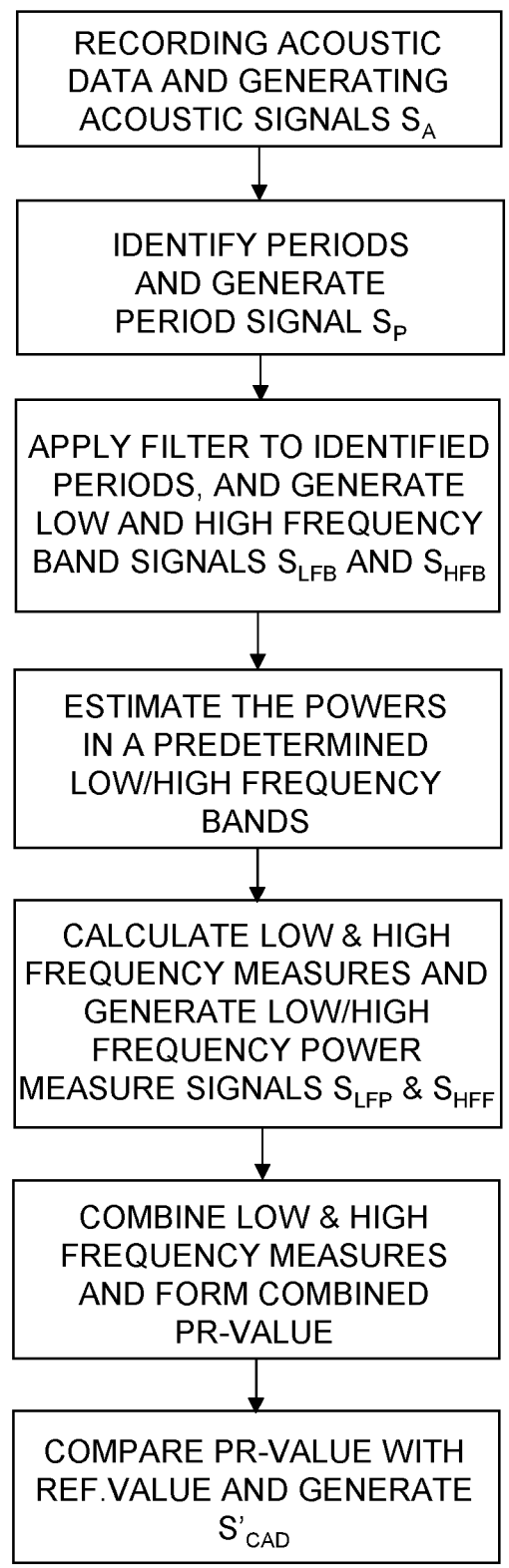
FIG. 12 shows a flow chart of a method according to another embodiment of the invention.

This embodiment will now be described with references to the flow diagram in FIG. 12. Thus, the method comprising:
recording acoustic data with said system having an acoustic sensor placed on the chest of a patient and generating acoustic signals $S_A$ indicating said data;
identifying diastolic or systolic periods in a predetermined time period of the stored acoustic data, and generating a period signal Sp indicating said identified periods;

applying at least one filter to the period signal Sp and generating a low frequency band signal $S_{LFB}$ indicating low frequency bands of said identified periods, and generating a high frequency band signal $S_{HFB}$ indicating high frequency bands of said identified periods;

estimating the power in said low frequency bands of said identified periods;

calculating a low frequency power measure based upon said estimated power, and generating a low frequency power measure signal $S_{LFP}$ indicating said low frequency power measure;

calculating a high frequency feature measure based upon an estimated feature in high frequency bands of said periods and to generate a high frequency feature measure signal $S_{HFF}$ indicating said high frequency feature measure, and combining said low frequency power measure and said high frequency power measure and comparing a resulting combined power ratio value with a further feature reference value for CAD to generate a combined risk-of-CAD-signal $S'_{CAD}$ indicating said risk in dependence of said comparison.

The recorded values may be affected by tissue damping factors such as BMI, gender, age or disease. The method comprises according to one embodiment the step of correcting said low frequency power measure against at least one tissue damping factor. How this can be made has been previously explained.

According to one embodiment, the method comprises the step of transmitting any of the aforementioned signals to an external unit for further processing or saving.

The invention also relates to a computer program product, comprising computer program instructions for instructing a computer system in a system or stethoscope to perform the steps according to the preceding method steps, when the data program instructions are executed on said computer system. The invention also comprises a computer program product, wherein the computer program instructions are stored on a computer readable medium.

The present invention is not limited to the above-described preferred embodiments. Various alternatives, modifications and equivalents may be used. Therefore, the above embodiments should not be taken as limiting the scope of the invention, which is defined by the appending claims.

The invention claimed is:

1. A system for detection of frequency power for diagnosing of coronary artery disease (CAD), comprising:
    an acoustic sensor adapted to be placed on the chest of a patient, and to generate acoustic signals $S_A$ that comprise a range of frequencies including a low frequency band and a higher frequency band;
    at least one memory adapted to store the acoustic signals $S_A$ from the acoustic sensor; and
    a control unit adapted to receive said acoustic signals $S_A$ from the memory;
    wherein the control unit further comprises:
        an identification unit adapted to identify diastolic or systolic periods in a predetermined time period of the stored acoustic signals $S_A$, and to generate a period signal $S_P$ indicating said identified periods;
        a filtering unit adapted to apply at least one filter to said identified periods and to generate a low frequency band signal $S_{LFB}$ indicating the low frequency band of said identified periods; and
        a calculation unit adapted to estimate the power in said low frequency band of said identified periods, and that said calculation unit is adapted to normalize said estimated power over the higher frequency band of the acoustic signals $S_A$, said calculation unit is further adapted to calculate a low frequency power measure based upon said estimated and normalized power and to generate a low frequency power measure signal $S_{LFP}$ indicating said low frequency power measure;
    wherein said system further comprising a risk determining unit adapted to determine a risk of coronary artery disease (CAD) by comparing said low frequency power measure with at least one reference value for CAD, and generating a risk-of-CAD-signal $S_{CAD}$ indicating the result of said comparison.

2. The system according to claim 1, wherein said low frequency band is between 5-70 Hz.

3. The system according to claim 1,
    wherein said calculation unit in addition is adapted to calculate a high frequency feature measure based upon an estimated feature in high frequency bands of said periods and to generate a high frequency feature measure signal $S_{HFF}$ indicating said high frequency feature measure and that said risk determining unit in addition is adapted to compare said high frequency feature measure with a further feature reference value for CAD and to generate a combined risk-of-CAD-signal $S'_{CAD}$ indicating said risk in dependence of said comparison.

4. The system according to claim 1, wherein said calculation unit is adapted to correct said low frequency power measure against at least one tissue damping factor, and that said tissue damping factor(s) is one or several of: BMI (Body Mass Index), gender, age and disease.

5. The system according to claim 1, wherein said acoustic sensor can be adapted to sense acoustic sounds down to 20 Hz.

6. The system according to claim 1 wherein said control unit is adapted to estimate the power by band pass filtering said identified periods using a 5-70 Hz band pass filter frequency and calculating the variance during said periods.

7. The system according to claim 1, wherein said calculation unit is adapted to estimate the power by generating a power spectrum directly or indirectly with at least one AR-model of said low frequency band and calculating the power in said low frequency band.

8. The system according to claim 1, wherein at least parts of said system being embodied by an electronic stethoscope.

9. The system according to claim 8 wherein the sensor, memory, control unit, identification unit, filtering unit, calculation unit, and risk determining unit are embodied by the electronic stethoscope and the system further comprising a transmitting unit also embodied by the electronic stethoscope, the transmitting unit being adapted to wirelessly communicate to an external unit at least one of the signals produced by the system.

10. The system according to claim 9 further comprising a display unit located within the electronic stethoscope that visually presents the patient's risk of CAD.

11. A method for detecting frequency power for diagnosing of coronary artery disease (CAD) using a system for detection of low frequency power, the method comprising:
    recording acoustic data with said system having an acoustic sensor placed on the chest of a patient and generating acoustic signals $S_A$ indicating said data, wherein the acoustic signals comprise a range of frequencies including a low frequency band and a higher frequency band;
    identifying diastolic or systolic periods in a predetermined time period of the stored acoustic data, and generating a period signal $S_P$ indicating said identified periods;

applying at least one filter to the period signal $S_P$ and generating a low frequency band signal $S_{LFB}$ indicating low frequency band of said identified periods;

estimating the power in said low frequency band of said identified periods;

normalizing said estimated power over the higher frequency band of the acoustic signals $S_A$;

calculating a low frequency power measure based upon said estimated and normalized power, and generating a low frequency power measure signal $S_{LFP}$ indicating said low frequency power measure, and comparing said low frequency power measure with at least one reference value for CAD, and generating a risk-of-CAD-signal $S_{CAD}$ indicating the result of said comparison.

12. The method according to claim 11, comprising estimating the power by band pass filtering said identified periods using a 5-70 Hz band pass filter frequency and calculating the variance during said periods.

13. The method according to claim 11, comprising estimating the power by generating a power spectrum directly or indirectly with at least one AR-model of said low frequency band and calculating the power in said low frequency band.

14. Method according to claim 11, comprising calculating a high frequency feature measure based upon an estimated feature in high frequency bands of said periods, and generating a high frequency feature measure signal $S_{HFF}$ indicating said high frequency feature measure;

comparing said high frequency feature measure with a further feature reference value for CAD and generating a combined risk-of-CAD-signal $S'_{CAD}$ indicating said risk in dependence of said comparison.

15. The method according to claim 11, comprising correcting said low frequency power measure against at least one tissue damping factor and that said tissue damping factor(s) is one or several of BMI (Body Mass Index), gender, age and disease.

16. A computer program product, comprising computer program instructions for instructing a computer system in a system to perform the steps according to the method according to claim 11, wherein the data program instructions are executed on said computer system, or wherein the computer program instructions are stored on a computer readable medium.

17. The method according to claim 11:

further comprising wirelessly transmitting to an external unit at least one of the signals produced by the method;

wherein the steps of recording, generating, identifying, applying, estimating, normalizing, calculating, comparing, generating a risk-of-CAD-signal, and transmitting are performed by a single electronic stethoscope.

18. The method according to claim 17 further comprising visually displaying the risk-of-CAD on the stethoscope.

* * * * *